United States Patent [19]

Wallis et al.

[11] 4,336,337
[45] * Jun. 22, 1982

[54] DETECTION OF BACTERIA

[75] Inventors: Craig Wallis; Joseph L. Melnick, both of Houston, Tex.

[73] Assignee: Baylor College of Medicine, Houston, Tex.

[*] Notice: The portion of the term of this patent subsequent to Sep. 30, 1997, has been disclaimed.

[21] Appl. No.: 159,785

[22] Filed: Jun. 16, 1980

Related U.S. Application Data

[63] Continuation-in-part of Ser. No. 23,737, Mar. 26, 1979, abandoned, which is a continuation-in-part of Ser. No. 945,197, Sep. 25, 1978, abandoned.

[51] Int. Cl.³ .................. C12M 1/12; C12Q 1/04; C12Q 1/06
[52] U.S. Cl. .................. 435/292; 23/230 B; 23/230 R; 422/58; 422/61; 422/69; 435/10; 435/34; 435/299; 435/810
[58] Field of Search .......... 422/55, 56, 57, 58, 422/69, 61; 23/230 B, 230 R; 435/30, 39, 40, 4, 29, 32, 33, 34, 36, 37, 243, 292, 293, 810, 38; 424/3, 7; 8/94.11

[56] References Cited

U.S. PATENT DOCUMENTS

| | | | |
|---|---|---|---|
| 2,167,304 | 7/1939 | Kloz | 422/56 X |
| 2,967,132 | 1/1961 | Sachs | 435/32 |
| 3,043,751 | 7/1962 | Goldman | 435/29 |
| 3,068,154 | 12/1962 | Majors | 435/39 |
| 3,245,882 | 4/1966 | Guthrie | 422/56 X |
| 3,415,718 | 12/1968 | Forkman et al. | 435/36 |
| 3,496,066 | 2/1970 | Berger et al. | 435/29 |
| 3,509,872 | 5/1970 | Trahan | 128/2 |
| 3,532,603 | 10/1970 | Freake | 435/39 |
| 3,568,627 | 3/1971 | Selinger et al. | 422/57 X |
| 3,621,016 | 11/1971 | Berger et al. | 260/240.1 |
| 3,681,027 | 8/1972 | Smith | 422/55 X |
| 3,783,105 | 1/1974 | Moyer et al. | 422/50 X |
| 3,846,242 | 11/1974 | Ernst | 435/32 |
| 3,891,507 | 5/1975 | Breuer | 422/56 X |
| 3,909,363 | 9/1975 | Bucalo | 23/230 B X |
| 3,923,463 | 12/1975 | Bagshuwe et al. | 422/66 |
| 4,004,453 | 1/1977 | Thyrum | 422/55 X |
| 4,153,675 | 5/1979 | Kleinerman | 422/56 X |
| 4,167,875 | 9/1979 | Meakin | 23/920 X |
| 4,225,669 | 9/1980 | Melnick et al. | 435/39 X |

FOREIGN PATENT DOCUMENTS

| | | | |
|---|---|---|---|
| 2401892 | 7/1975 | Fed. Rep. of Germany | 422/55 |
| 1329823 | 9/1973 | United Kingdom | 422/56 |

Primary Examiner—Barry S. Richman
Attorney, Agent, or Firm—Fulbright & Jaworski

[57] ABSTRACT

A test substrate, including a semi-permeable membrane which retains bacteria on the membrane and which has a net positive surface charge to permit coloring of bacteria thereon with a cationic dye, without the membrane adsorbing substantial amounts of said dye. Substrate is included in a kit for detecting bacteria.

9 Claims, 4 Drawing Figures

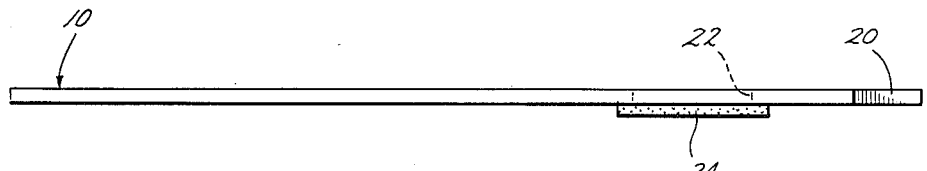

DETECTION OF BACTERIA

This invention is a continuation in part of U.S. Application Ser. No. 23,737, filed on Mar. 26, 1979, now abandoned, and a continuation-in-part of U.S. Application Ser. No. 33,900 filed on Apr. 27, 1979 now U.S. Pat. No. 4,225,669 issued on Sept. 30, 1980, which application is a continuation-in-part of U.S. Application Ser. No. 945,197, filed on Sept. 25, 1978, now abandoned.

A need exists for a method of rapidly detecting bacteria in fluids from many sources. Of particular significance is the need for rapid detection of pathogenic bacteria in physiological fluid specimens, such as blood, urine and the like. Moreover, a need exists for a method for rapidly determining the susceptibility of such infecting bacteria.

A further need exists for the dection of bacteria in other systems, for example, aqueous systems.

Urine specimens in general form the major part of the work load of the diagnostic microbiology laboratory. By far the most common urological disease is urinary tract infection. In fact, in many hospitals, bacteriuria is the most common form of nosocomial infection, often following the use of in-dwelling catheters and various surgical procedures. The volume of specimens requiring bacteriuria screening is further increased by the need to repeat the tests to insure accurate diagnosis where their reliability may have been reduced due to contamination of the specimen during collection. A further problem with diagnosis and treatment of bacteriuria is the frequent lack of correlation between a patient's symptomatic response to antimicrobial treatment and successful treatment. In order to insure that the prescribed antimicrobial agent is in fact effective, repeated tests during therapy are required. The need for simple, rapid bacteriuria tests is thus clear. Moreover, in view of the frequent unsuspected asymptomatic occurrences of urinary tract infections among children, pregnant women, diabetics and geriatric populations, diagnosis of which may require collection and testing of several specimens, bacteriuria tests must be sufficiently simple and economical to permit routine performance. A need thus exists for rapid, inexpensive screening tests to facilitate diagnosis and insure proper treatment of urinary tract infections.

Rapid tests for detection of bacteria in blood are also needed, in view of the high mortality rate associated with septicemia and bacteremia. Prompt detection of the disease permits early administration of an appropriate antibiotic thus greatly improving the chances for survival.

According to conventional techniques, bacterial infections in specimens, such as blood, urine, spinal fluid and the like, are detected by diluting a specimen with culture media and incubating the diluted specimen at 36° C. The appearance of turbidity manifests bacterial growth. However, relatively extended periods of incubation are required since turbidity due to bacterial growth is difficult to distinguish from turbidity due to the presence of blood cells or contaminants in the specimen and from turbidity caused by precipitate formation. Substantial increases in turbidity following incubation periods of about 24 hours indicate bacterial growth.

Another very important procedure in the clinical laboratory is determination of antimicrobial susceptibilities. The principal methods presently employed to determine susceptibility of a micro-organism to an antibiotic include dilution tests, such as the broth tube and agar plate procedures, and agar diffusion tests, utilizing antibiotic-impregnated discs. Typically, such methods require incubation periods of 16 to 18 hours before the inhibitory effect of an antimicrobial agent can be accurately assessed. Furthermore, such tests often are time consuming, relatively expensive and must be performed by skilled laboratory personnel.

Although staining techniques are known in clinical microbiology, such techniques are typically employed to stain dried bacterial smears on slides rather than in fluid specimens. In the practice of such prior art staining techniques, a dried bacterial smear on a slide is treated with a reagent which stains the bacteria in a manner which permits ready microscopic examination thereof. Thus, expensive equipment and skilled microbiologists are required to perform such analyses.

In addition to bacterial examination of body fluids, it is often necessary to analyze the bacterial content of other fluid specimens, such as water and pharmaceutical products. The need for rapid, simple, inexpensive and accurate methods for detecting and analyzing bacteria in body fluids and other fluid specimens is thus evident.

In other systems, it is also beneficial to rapidly detect bacteria. For example, in cooling water systems; e.g., as used in cooling towers, it is necessary to determine bacterial content in order to ascertain appropriate treatment, as with an appropriate biocide.

It has now unexpectedly been discovered that both gram-negative and gram-positive living bacteria can be stained for simple, rapid analysis by means of the present invention. Concentrated bacteria stained with the composition are readily visible and can thus be rapidly detected without resort to microscopic examination or specially trained personnel. Moreover, antimicrobial susceptibility of bacteria can be determined rapidly and simply by means of the present invention. Further, it was unexpectedly found that inexpensive, simple and rapid quantitative analyses of bacteria are possible employing the present invention Finally by means of the present invention, it is possible to differentiate gram-negative and gram-positive bacteria.

The present invention is directed to an improved article and kit for use in the rapid detection of bacteria.

In accordance with one aspect of the present invention, there is provided an article for use in the detection of bacteria comprised of a test substrate including a flow through semi-permeable membrane for a test sample which includes or is suspected of including bacteria, which membrane has a pore size which retains bacteria on the membrane, with the membrane having a net positive electrostatic surface charge to permit coloring of bacteria thereon without adsorbing substantial amounts of the dye.

In accordance with a preferred embodiment, the substrate includes color differentiating indicia for providing a reading of bacterial concentration corresponding to color retained on the membrane.

In accordance with a particularly preferred embodiment, the test substrate is a card having an aperture, with the semi-permeable membrane covering the aperture. It is to be understood, however, that all or a portion of the test substrate may be comprised of the semi-permeable membrane.

In accordance with a further aspect of the invention, there is provided a test kit comprised of the test substrate and a chelating agent operative in the basic pH range and a basic dye capable of staining bacteria at a basic pH. Bacteria are stained when contacted with the composition at a pH above about 7.0. Bacteria which are stained with the composition on the test substrate become readily visible, and may thus be detected.

Semi-quantitative analysis of bacteria may be accomplished by comparing the gradation of color developed in the stained bacteria on the test substrate, with a nomograph or other calibrated standard. Semi-qualitative analysis of the stained bacteria may be effected by means of an organic acid wash having a pH of about 2.5 or 2.6, since such an acid wash will completely decolorize only gram-positive bacteria stained with the composition.

By incubating bacteria with an antimicrobial agent prior to staining with the composition of the invention, the susceptibility of the bacteria to the agent can be determined. The relative intensity of the color of stained, concentrated bacteria, thus treated, will be related to the effectiveness of the agent employed.

The invention is particularly useful in laboratory screening of body fluids and other physiological fluid specimens, and for detection of bacteria in aqueous systems.

Since the color intensity of stained bacteria on the substrate is correlated with the number of bacteria in a sample, semi-quantitative analysis of bacteria may be accomplished by comparing the intensity of the color developed in the stained concentrated bacteria with a nomograph or other known standard. When concentration of the bacteria is effected by deposition of bacteria on the semi-permeable membrane, dye not associated with the bacteria, which may remain on the substrate and which may interfere with an accurate detection and quantitation of bacterial presence, may be removed by means of an organic acid wash having a pH in the range of about 2.7 to 4.0. If bacteria are incubated with an antimicrobial agent for a brief period prior to contact with the staining composition, the susceptibility of the bacteria to the agent is determined by comparing the color intensity of the stained, concentrated bacteria with a control. Differentiation of the gram-stain of bacteria may be effected by treating the stained bacteria with an organic acid wash having a pH of about 2.5–2.6. Gram-positive bacteria are completely decolorized by such a wash whereas stained gram-negative bacteria are not.

The invention has particular application to the detection and analysis of bacteria in physiological fluid specimens, particularly urine specimens and also in aqueous systems.

More particularly, it has been discovered that the combination of a chelating agent, operative in the basic pH range, and a dye, capable of staining bacteria at a pH above about 7.0, results in a composition having the capacity to stain both gram-negative and gram-positive bacteria. In the absence of the chelating agent, dyes, particularly basic dyes, fail to stain gram-negative bacteria. Bacteria may be stained simply by contacting the bacteria on the semi-permeable membrane of the test substrate with the chelating agent/dye composition at a nearly neutral or basic pH.

Any dye capable of staining bacteria at a basic or neutral pH may be employed in the composition and method for staining bacteria described herein. Since the staining operation is effected at a pH of about 7 or higher, the dyes used must be operative in this pH range. As a general rule, basic or cationic dyes are effective bacteria stains in the practice of the present invention. Specifically, safranin-O, toluidine blue, methylene blue, crystal violet and neutral red may be utilized in the present invention, with Safranin-O being particularly preferred. The dye is preferably chromatographically purified prior to use thereof to remove impurities which may stain the membrane.

The chelating agents which may be employed in the practice of the present invention are also limited to those which are operative at the pH at which the staining is effected, that is, about 7.0 or higher. Salts of ethylenediaminetetraacetic acid (EDTA) and citric acid may be utilized. In particular various sodium salts of these two acids are effective, specifically the di- and tetrasodium salts of EDTA and the di- and trisodium salts of citric acid. Tetrasodium EDTA is a particularly preferred chelating agent.

The amounts of chelating agent and dye necessary to effectively stain bacteria range from about 0.001 to about 0.1 molar (M) chelating agent and 1:1000 to 1:300,000 dilution of dye. These amounts are calculated as final concentrations, taking into account any dilution due to the material in which the bacteria may be present.

The specific concentration of dye and chelating agent utilized may be dependent in part upon the condition of the bacteria when contacted with the staining composition. For example, where the staining is effected on bacteria which are relatively concentrated or free of interfering substances, competing chemical or physical reactions will as a rule be reduced and more concentrated compositions may be employed. On the other hand, where the bacteria are dispersed in a fluid medium containing other materials, it may become necessary to adjust the concentration of dye and/or chelating agent upward or downward to compensate for reactions with these additional materials. For example, in urine specimens, reduced concentrations of dye should be used to avoid formation of precipitates with urine compounds which occurs at 1:1000 dye dilution. In general, dye dilution on the order of 1:2500 or more is adequate to avoid such precipitate formation, but dilution of 1:10,000 or more is preferred. In general, particularly effective bacteria staining can be accomplished employing compositions comprising about 0.05 M chelating agent and 1:1000 or higher dye dilution with relatively pure or concentrated bacteria or 0.05 M chelating agent and 1:10,000 or higher dye dilution where the bacteria is fluidized with interfering materials.

In practice, the staining composition may be stored in concentrated form. For example, sterile Safranin-O and EDTA could be stored at the following concentrations: Safranin, 1:1000; EDTA $Na_4$, 0.5 M. At the time of use, this mixture could be diluted to the desired concentration. For example, 1 ml could be added to 9 ml of test material to obtain a final concentration of 1:10,000 Safranin and 0.05 M EDTA. The storage stability of the staining composition is increased when the dye used to make the composition has been solubilized in undiluted organic media.

As indicated above, the composition is effective to stain both concentrated bacteria and fluidly suspended bacteria; however, in accordance with the invention the staining is effected on a semi-permeable membrane. The bacteria is deposited on the semi-permeable membrane of the test substrate. Thereafter, staining of the bacteria is effected by pouring a solution of the composition through the membrane.

The degree of staining is somewhat dependent upon concentration of dye and time of contact. With higher concentrations, the period of contact may be reduced; conversely with lower concentrations of dye, increased holding times are required. Further, the time of contact is inversely related to the temperature at which the contact is effected. For example, optimal staining of bacteria in fluid specimens with a dye dilution of 1:5000 requires holding time of 45 minutes at 4° C., 15 minutes at 25° C., 5 minutes at 37° C. and 1 to 2 minutes at 50° C. In general, at least 15 minutes at room temperature is required to obtain maximum staining of bacteria in urine specimens; after 30 minutes, no further staining is observed. However, if the bacteria is concentrated on semi-permeable membranes prior to staining as in the present invention, periods of as little as 15–60 seconds are required, since staining compositions having a 1:1000 dye dilution may be employed.

The concentration of bacteria which can be detected by this staining procedure varies somewhat with the type of bacterium, but in general gram-negative bacteria can be detected at levels of $10^5$ CFU/ml, whereas detection of gram-positive bacteria may require accumulation of $10^6$ CFU/ml. Of course, smaller concentrations of bacteria can be detected by concentrating larger quantities of fluid.

Sedimentation and filtration are examples of effective means for concentrating bacteria. When sedimentation is employed, bacteria present in the specimen will be manifested by a precipitate having the color of the dye employed. With filtration techniques, bacteria are deposited on semipermeable membranes whereupon their presence is evidenced by the color of the dye developing on the membrane.

Conventional procedures, such as centrifugation may be employed to effect sedimentation. For example, bacteria in a 100 ml physiological fluid specimen could be sedimented at 3000 rmp for 15–30 minutes in a conventional chemical centrifuge, after being contacted with the composition of the invention. A pellet in the tube having the color of the dye used indicates the presence of bacteria.

In accordance with the invention the semi-permeable membrane has a pore size sufficient to retain bacteria. In general, membranes having a pore diameter of about 0.2 to 1.0 μm may be employed. The membrane does not have a net negative electrostatic surface charge; i.e., it has a net positive electrostatic surface charge. The relative suitability of membranes can be evaluated by simply passing the appropriate concentration of the dye being used through the various membranes and comparing the intensity of color developed. A preferred membrane is formed of epoxy-fiberglass.

The use of the net positive electrostatic surface charge functions to reduce or eliminate the retention of dye on the membrane per se, whereby the dye is retained by the bacteria on the membrane to provide an indication of bacterial concentration; the dye retained increases with the amount of bacteria on the membrane which is indicative of the bacterial concentration of the test sample.

The preferred membrane is one that has essentially only a positive electrostatic surface charge; i.e., essentially no net negative charge. If the membrane includes some negative surface charge, the membrane may be treated with a cationic agent; e.g., a cationic detergent to reduce or eliminate the negative charge. Suitable cationics are, for example, quaternary ammonium salts.

In accordance with a preferred aspect, the test kit also includes an acid which is used as a decolorizing wash for removing dye, if any, retained by the membrane. The acid wash decolorizes the membrane with little, if any, decolorization of the stained bacteria. The wash is generally an organic acid, such as citric or acetic acid. The acid is generally used at a pH of from about 2.7 to 4.0. pH's below about 2.7 should be avoided since decolorization of stained bacteria may also occur. Acetic acid at a pH of about 3 is a preferred wash.

The dye may be solubilized in water for use in the test. In most cases, the dye should be chromatographically purified for such purposes. The dye may also be solubilized in an organic media; e.g., an organic media for culturing bacteria.

A preferred combination for maximizing removal of free dye adsorbed by membrane surfaces is as follows: a fiberglass-epoxy filter having a net positive electric surface charge (in particular one having essentially no negative surface charge) and particularly one having the pore and flow properties of the G-2 series sold by Finite Filter Corp. (Detroit, Michigan), acetic acid at a pH of about 3 and the cationic dye, preferably Safranin-O, solubilized in undiluted bacteria culturing media or water, preferably water. Substantially all free dye on a membrane surface is decolorized when this combination is employed in the practice of the present invention.

The decolorizing acid wash may be effected simply by contacting the colored surface of the membrane with the acid for a short period and thereafter suctioning or otherwise removing the wash from the membrane. The optimum time and number of washes can be determined by simple trial and error control runs. Typically, with an acid at pH 3, 1 to 3 washes for a period of less than five minutes each will be sufficient.

The presence of bacteria can be semi-quantitatively detected employing the present invention. Such a quantitative analysis can be accomplished by simply staining and concentrating the bacteria on the test substrate as above described. The intensity of the color of the stained, concentrated bacteria, which correlates with the bacterial population, can then be compared with a standard which has been calibrated using known bacterial amounts. Conventional techniques, such as nomographic, colorimetric and photometric procedures, may be employed to make the analysis. Bacterial growth in fluids may be measured using the above methodology by comparing the intensity of bacterial stains developed in samples drawn from the fluid at different time intervals. In accordance with a preferred embodiment, suitable color indicia corresponding to bacterial concentration are included on the test substrate whereby, the concentration of bacteria in the sample can be conveniently determined by comparing the color of the stained bacteria on the semi-permeable membrane with the color indicia.

Differentiation of the gram-stain of bacteria may also be accomplished employing the present invention. As noted above, organic acid washes below a pH of about 2.7 tend to decolorize stained bacteria as well as free dye on a membrane surface. However, if the pH of the acid is maintained at about 2.5 to 2.6, gram-positive bacteria are totally decolorized; below a pH of about 2.5 both gram-positive and gram-negative bacteria are decolorized. It is thus possible to differentiate gram-negative and gram-positive bacteria. Thus, by means of an organic acid wash, of the type used to decolorize free dye on a membrane, but having a pH reduced to about 2.5 to 2.6, a semi-qualitative analysis of bacteria stained with the composition of the invention can be performed.

By means of the present invention, it is also possible to determine antimicrobial susceptibilities of bacteria. Treatment of bacteria with an antimicrobial agent to which they are susceptible prior to contact with the staining composition will result in a diminution in number of bacteria. Consequently, the color of the stained concentrated bacteria thus treated will be less intense than that of resistant cultures or an untreated control. The reduction in color will be roughly parallel to the degree of susceptibility to the antimicrobial agent. Thus, when bacteria are treated with an antimicrobial agent prior to contact with the staining composition of the invention, the intensity of the color of the stained, concentrated bacteria will be related to the susceptibility of the bacteria to the agent. Treatment of bacteria with an antimicrobial agent having a bacteriostatic or bactericidal effect prior to staining will result in the color intensity of the stained concentrated bacteria being comparatively less than that of stained concentrated bacteria which were not treated with the agent. By comparing the colors developed in bacteria which have been treated with different antimicrobial agents or different amounts of a single agent, the relative inhibitory effects thereof can be evaluated.

Treatment of bacteria with an antimicrobial agent can be effected simply by contacting either concentrated or fluidly suspended bacteria with the agent generally for no more than about 1 to 3 hours. The procedure may be employed with bacteria in a fluid specimen or with colonies of bacteria from a culture plate which have been suspended in an organic broth. The amount of agent employed in this procedure will be in accordance with known standards, such as standardized FDA approved antimicrobial discs.

If desired, a bacteria sample may be incubated prior to treatment with antimicrobial agents. Incubation will enhance the accuracy with which susceptibility to the agents is determined due to the culture reaching log phase of growth. Since bacteria grow at a rapid rate when incubated at 35°–36° C., bacterially infected samples need be incubated for only about 30 minutes to 1 hour to insure highly accurate results. Such incubation is desirable where the relative inhibitory effects of several antimicrobial agents having similar activities are being assessed.

The present invention has particular application to the staining and analysis of bacteria in physiological fluid specimens and in aqueous specimens, e.g., industrial waters, such as cooling tower water; swimming water, drinking water, and the like. For example, urine, which has been clarified conventionally, may be treated with a solution containing 1:10,000 Safranin-O solubilized in nutrient broth and 0.05 M tetrasodium ethylenediaminetetraacetate. The urine is then passed through a test substrate including a semi-permeable membrane having a net positive charge as hereinabove described whereupon the stained bacteria are readily visible. If desired, the filter is then washed with pH 3 acetic or citric acid.

Alternatively, and preferably, the urine may be passed through the semi-permeable membrane of the test substrate which results in the deposition of the bacteria in the urine onto the membrane surface. Thereafter, the deposited bacteria are treated with sufficient 1:1000 basic dye—0.05 M EDTA salt mixture to cover the membrane surface. After 15–60 seconds, or longer if desired, the dye is drawn through the membrane by suction. If desired, the membrane may then be washed with pH 3 acetic acid.

In some instances, urine of patients suffering with bacteriuria may have precipitates which clog membranes used in the practice of the present invention. Such urine is first clarified, for example with a 5 $\mu$m clarifier, to remove the precipitates and enhance filtration of the urine. Occasionally, urine may contain gram-positive bacteria in the form of aggregates which are removed by the 5-$\mu$m clarifier. Without clarification, such urines would not be able to be processed by the bacteriuria-detection method of the invention.

In order to increase the flow rates of urine through the 0.65-$\mu$m filters employed in the present method, the sediments, such as urates, present in the urine may be solubilized. Acetic acid is the optimal solvent for this purpose. Urine specimens mixed with equal volumes of acetic acid at pH levels of 2.0, 2.5, 3.0, 3.5 and 4.0 exhibit increased optical transmission at 540 nm only at pH 2.5 or lower. Further, mixtures of pH 2.5 acetic acid and urine attain a final pH between 3.5 and 4.5 in most cases and are not deleterious to the staining reaction of bacteria (i.e., the bacteria retained their ability to react with safranin).

The acetic acid diluent enhances the flow rates of urines. In many instances, the staining intensity is greater in the acetic acid diluted urines than in corresponding specimens without acetic acid. This is believed to be due to the fact that suspended solids which are solubilized can no longer impact on the entrapped bacteria on the filter and prevent staining.

Although the acetic acid diluent described above aids flow rates of urines which contain solids, heavily pigmented urines containing soluble organics often clog membranes because of the adsorption of the pigments to the 0.65-$\mu$m filters. Among anionic exchangers which remove urine pigments, Exchanger A109-D (Diamond Shamrock, $Cl^{31}$ charged) is the resin of choice since it renders the urine almost colorless. Flow rates of urines through 0.65-$\mu$m filters are dramatically increased if the urine is first passed through the anionic resin. Urines may be processed employing such a resin as follows: 3 ml of a urine specimen is passed through 5-gram resin column resulting in recovery of 2.5 ml of the specimen in the resin filtrate. This filtrate is then mixed with an equal volume of acetic acid diluent and processed through the filter, stained and washed as previously described.

Resin treatment in this manner enhances rapid filtration of the sample through filters. The average flow rate of such samples is 0.2 minutes. Also some positive bacteriuria samples which may appear negative without resin treatment, will produce positive results when the resin is used. Additionally, urines which clog filters without resin treatment will pass them more easily after the resin treatment.

Incorporation of the resin treatment into the method of the invention may be accomplished as follows: Elkay filters (serum separators), which are 10-ml plastic tubes with filters (30–40 m) at the butt of the tube and a skirt protruding around the butt which forms a seal when the separator, are loaded with 5 grams of resin suspended in water containing 1:250 formalin and are placed in 16-mm test tubes each of which contains 2.5 ml of pH 2.5 acetic acid. The fluid phase of the resin suspension is then drawn off by vacuum, leaving a moist resin column within the separator. The residual formalin maintains the sterility of the column. The separator is then placed in the 16-mm tube containing the acetic acid by forcing the butt of the Elkay tube into the 16-mm tube and driving the plastic tube into the acetic acid. Tubes may be thus prepared prior to use and stored in this manner. At the time of use, 3.0 ml of urine is added to the Elkay tube (which has about 4.5 ml of reservoir volume above the resin column). The Elkay tube is then gripped and removed slowly from the test tube. This action produces a vacuum in the test tube because of the Elkay skirt against the sides of the tube, thus drawing the urine through the resin and into the acetic acid. The end result is a 5-ml sample containing the urine and acetic acid, which may then be filtered, stained and washed in accordance with the method of the invention.

Although the acetic acid diluent and the resin exchanger increase the efficiency of the bacteriuria-detection method, there are still occasional urines which give problems due to the presence of pigments that are not removed by the anionic resin exchanger. Blood, hemoglobin, certain basic drugs, and basic pigments present in urine of patients with certain pathologic disorders will coat the 0.65-μm filter and prevent staining of the bacteria. For example, when urine containing blood is processed, the erythrocytes pass the resin (since cells cannot exchange with resin). When mixed with acetic acid, the blood cells are lysed and the basic hemoglobin is concentrated onto the filter in the form of a greenish pigment, which interferes with the staining of bacteria. However, when such filters are treated with hydrogen peroxide, the problem is resolved. A 30-second treatment of a filter containing hemoglobin with 0.2 ml of 30% $H_2O_2$ completely clears the filter of color. Staining of the filter with safranin-EDTA and subsequent washing indicate that the peroxide has no effect on the stainability of the bacteria. In fact, peroxide treatment of bacteria often enhances the staining. Therefore, in all cases where filters manifest excess pigment (after processing through the resin and acetic acid) on 0.65-μm filters, they may be treated with $H_2O_2$ as described above for 30 seconds. Thereafter they are stained and washed as described earlier in this application.

Occasionally, very turbid, bloody or dark amber urines will deposit a precipitate or pigmented compound on the membrane. Staining of this material may lead to false-positive results. In those cases where urine samples are so heavily contaminated with precipitates, such as phosphates, carbonates, urates or blood, it may be possible to employ the methods of the present invention if the specimen is centrifuged at low speeds whereby these materials are sedimented without sedimentation of bacteria. Centrifugation at speeds on the order of 500 rpm are generally effective for this purpose. As a result of such centrifugation, the bacteria-containing supernatant will more readily pass through the filter. This procedure will reduce false-positives and will uncover positives that may be masked by the excess pigment deposits.

The test substrate also functions to concentrate the bacteria present in the sample into a small area, which facilitates the ability to determine the bacteria concentration in accordance with the overall kit of the present invention. In general, the sensitivity is increased by increasing the ratio of sample volume to test area. As a result of the net positive electrostatic surface charge, the semi-permeable membrane does not attract the cationic dye employed for staining which minimizes or eliminates the retention of stain by the membrane, whereby the stain is retained essentially only by the bacteria which remain on the membrane.

In employing the present invention for determination of bacteria in aqueous systems, such as cooling water systems, the test kit may include, in addition to the test substrate, dye, chelating agent and acid decolorizing wash, one or more of an anionic exchange resin; rust solvent and filter paper. The anionic exchange resin and rust solvent are employed to remove impurities from the water which may adversely affect the ability to read the color stain on the semi-permeable membrane. Thus, for example, the rust solvent is a material which solubilizes ferric oxides and hydroxides to prevent coloring of the test membrane. A suitable rust solvent is a sodium bisulfite-sodium thiosulfite mixture. The rust solvent may be employed after concentrating the bacteria on the membrane, followed by use of the acid decolorizing wash.

The anionic exchanger may also be employed for pretreating the water sample (prior to passage through the membrane) in order to remove various pigments which may be present in the water.

The invention will be further described with respect to the accompanying drawing wherein:

FIG. 1 is a plan view of a testing card provided by the present invention and used in carrying out the testing procedure of the present invention.

FIG. 2 is a side elevational view of the card shown in FIG. 1.

Throughout the following description, like reference numerals are used to denote like parts in the drawings.

DESCRIPTION OF THE PREFERRED EMBODIMENTS

Figure 3:
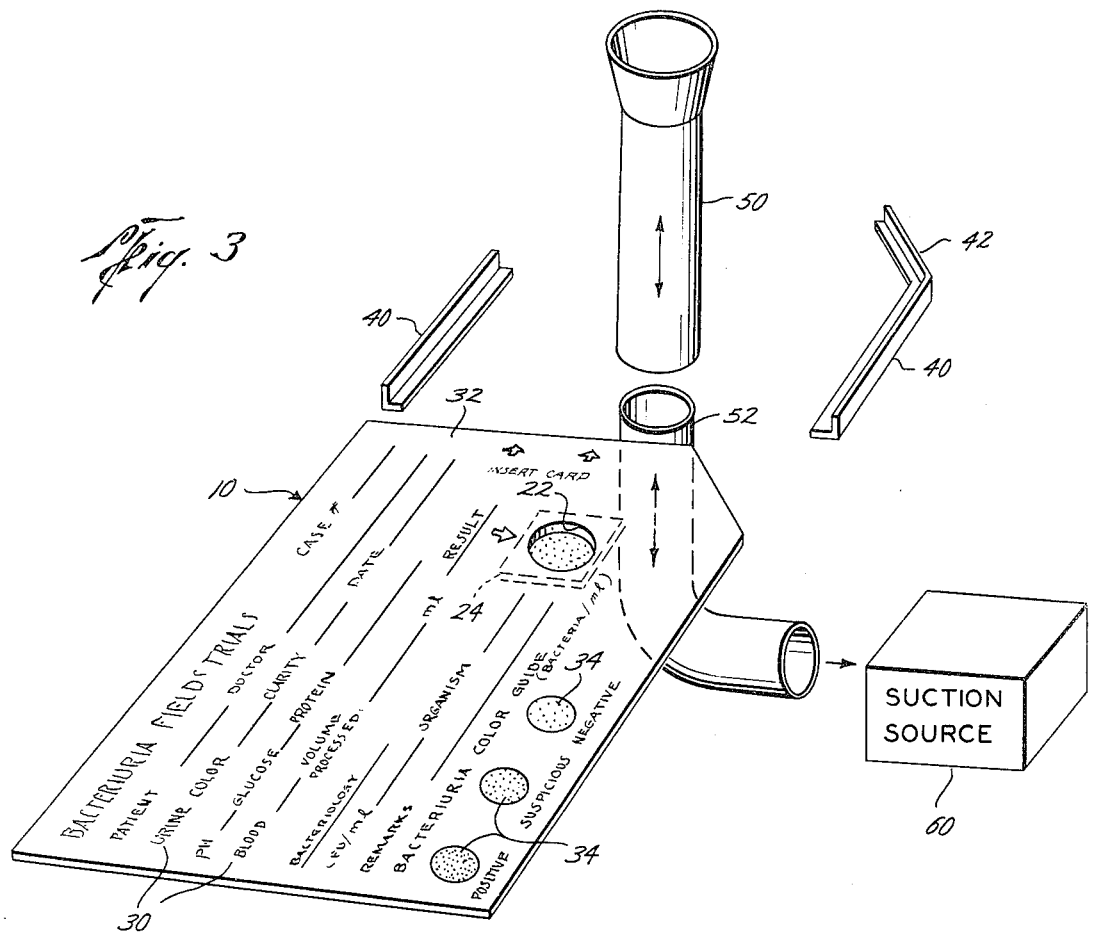
FIG. 3 is a diagrammatic depiction of the manner in which the card is inserted intermediate conduit segments which are thereafter brought into fluid-tight engagement communicative with the filter component in the card so that the fluid to be tested can be force transferred from one conduit segment through the filter component and into the other conduit segment.

The method of the present invention will be described in the following detailed description in connection with its utilization for detecting the presence of bacteria in urine, although it will be understood that as indicated above, the method of the invention is applicable to testing of a wider range of fluids and for detecting various of the components formed in such fluids.

With reference now to FIGS. 1 and 2, the present invention provides a test substrate, which as particularly shown in the form of a test card 10 which is an elongated paper board or cardboard component (although often materials such as, e.g., thermoplastic could also be used) having elongated longitudinal side margins as at 12 and 14 and transverse end margins 16 and 18. One corner of the card as at 20 is formed with a cutaway portion which in conventional manner can be employed for locating the card against a stop abutment in a reception device such as a testing machine to accurately position the card as a precedent to passing a test sample through the filter component to be described shortly. Disposed within the structure of the card is a through aperture 22 and which is overlayed (at the underside face of the card) by a semi-permeable membrane or filter 24 of the type hereinabove described securely attached to the card structure.

The card 10 also bears on its upper face 32 printing indicia 30 of various character which can be employed for recording certain data consequent from performing the test and also for maintaining a permanent record of the testing procedure. The upper face of the card includes an indicium guide in the form of a plurality of indicia markings 34 printed in varying coloration intensities from lightest to darkest of a particular color associated with the coloration of the filter component upon completion of the test and which indicium guide is used to make a comparative analysis of the quantum of presence of the particular component, in the body or other fluid.

FIG. 3 depicts diagrammatically a section of a testing machine as could be present in a doctor's office, clinic, laboratory facility or the like, and employed in conjunction with the test card for carrying out a test to produce a semi-quantitative analysis or approximate determination of the amount of bacteria present in urine or other fluid. A similar apparatus could be used in the field for determination of the amount of bacteria in cooling tower, industrial, drinking, and swimming pool water.

The card 10 is inserted in the machine structure, which could, for example, be provided with a pair of card reception rails 40 including a stop abutment 42 for nesting thereagainst of the cutaway edge 20 on the card, such engagement of edge 20 with the stop abutment 42 ensuring that the aperture 22 in the card will be axially aligned with a pair of opposed axially aligned conduit segments 50 and 52 in the machine. When it is desired to effect testing, the conduit segments 50 and 52 are stroked axially as indicated by the arrows to bring them together and into fluid-tight communicative engagement with the filter component 24 on opposite sides thereof. The urine specimen or other sample to be tested and which has been stained with a chelating agent and dye, as hereinabove described is then introduced to the upper conduit segment 50. It may be allowed to remain therein for a short period following which, a suction force from a source thereof as at 60 is applied to the other conduit segment 52 which in consequence results in transfer of the sample through filter component 24 into the other conduit segment, the stained bacteria present in the body fluid being retained in the filter component which is provided as a semi-permeable membrane having a pore size of 0.2 to 1.0 μm.

The amount of bacteria retained as a concentration thereof in the filter component 24 will give evidence of its presence by a particular coloration of the filter. For example, the coloration should be of pink hue. By comparing the appearance of coloration in the filter component with the indicium guide markings 34, (which, e.g, could range in appearance from light pink to dark red) it is possible to match the observed filter concentration appearance with that of the guide to provide an approximate determination of the amount of bacteria which is present in the test sample. It will be noted that in this regard, the indicium guide also could be provided with designations as to 70 indicating whether the bacteria level (in terms of bacteria per milliliter) associated with a particular coloration reflects a positive, a negative or a suspicious test result. This last "suspicious" characterization is intended to reflect a result intermediate a clear positive and a clear negative result, possibly warranting a retest or further more refined testing.

The test substrate particularly described with reference to the drawings, may be modified within the spirit and scope of the invention. Thus, for example, the substrate may be in a form other than a card, provided that the substrate includes a semi-permeable membrane of the type hereinabove described (pore size to retain bacteria and a net positive electrostatic surface charge).

Figure 4:
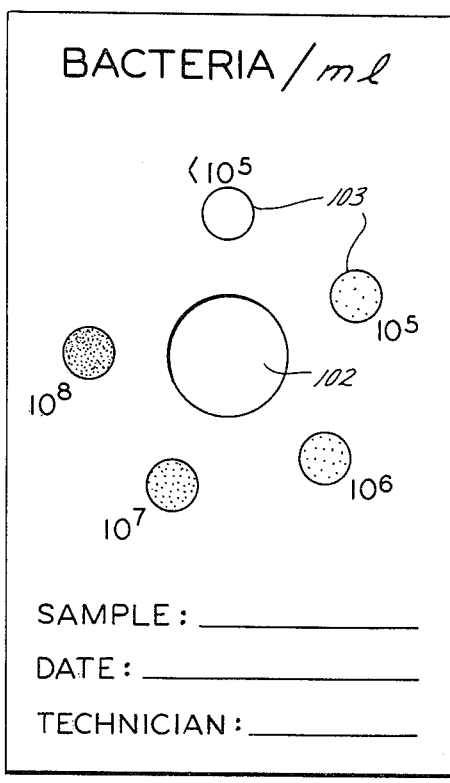
FIG. 4 is a plan view of another embodiment of a test card.

Thus, for example, the test substrate may take the form of a card as shown in FIG. 4. Referring to FIG. 4, the card 101 is provided with an aperture with the aperture being covered by a semi-permeable membrane 102 of the type hereinabove described. The card 101 is further provided with a color indicia, in the form of six colored circles 103 of gradated color ranging, for example, from a very light color to a darker color, with the darker colors corresponding to increased bacterial concentration. As shown, the bacterial concentration for each of the color marks corresponds to bacteria concentration of $<10^5$, $10^5$, $10^6$, $10^7$ and $10^8$. The card further includes an area for recording pertinent sample information.

The test substrate is employed as hereinabove described, with the color remaining on the bacteria being compared with the color indicia in order to determine the bacteria concentration in the sample. Thus, for example, in using the card for the testing of water, the water sample is passed through a column containing an anionic exchange resin for removing pigments from the water sample and then through the membrane 102 on the test card 101 to concentrate any bacteria present in the water sample on the membrane 102. Rust solvent; e.g., sodium bisulfite-sodium thiosulfite dissolved in acetic acid is then passed through the membrane to remove any pigmentation which may have been caused by iron compounds in the water sample. The acid decolorizing wash, in particular, acetic acid is then passed through the membrane to remove any remaining rust solvent. The cationic dye and chelating agent is then passed through the membrane, followed by washing with the acid decolorizing liquid to complete removal of any dye which may adhere to the membrane. The color of the stained bacteria remaining on the membrane is then compared with the color indicia to ascertain the concentration of bacteria in the sample.

The present invention is particularly advantageous in that bacteria can be easily determined in a wide variety of fluids and in particular body fluids and aqueous fluids.

Numerous modifications and variations of the present invention are possible in light of the above teachings and therefore, within the scope of the appended claims the invention may be practised otherwise than as particularly described.

We claim:

1. A kit for detecting bacteria, comprising:
    (a) a cationic dye for staining bacteria at a pH of above 7.0;
    (b) a chelating agent effective at a pH of above 7.0;
    (c) an acid decolorizing wash at a pH of from 2.7 to 4.0; and
    (d) a test substrate, said test substrate including a semi-permeable membrane which permits a test sample including bacteria to flow therethrough and which has a pore size to retain bacteria in the sample on the membrane for coloring thereon, said semi-permeable membrane having a net positive electrostatic surface charge to permit coloring of bacteria thereon with a cationic dye, without the membrane absorbing substantial amounts of said dye, the substrate including color differentiating indicia for providing a reading of bacterial concentration corresponding to color retained on the membrane.

2. The kit of claim 1 and further comprising a rust solvent for dissolving rust.

3. The kit of claim 1 wherein the test substrate is a card having an aperture, said semi-permeable membrane covering said aperture.

4. The kit of claim 3 wherein the semi-permeable membrane is essentially free of negative electrostatic surface charge.

5. The kit of claim 4 wherein the semi-permeable membrane is an epoxy-fiberglass membrane.

6. The kit of claim 4 wherein the dye is safranin-O.

7. The kit of claim 6 wherein the chelating agent is a salt of ethylenediaminetetraacetic acid.

8. The kit of claim 6 wherein the dye is chromatographically purified safranin-O dissolved in water.

9. The kit of claim 8 wherein the acid decolorizing wash is comprised of acetic acid.

* * * * *